United States Patent
Swain et al.

(10) Patent No.: US 7,144,753 B2
(45) Date of Patent: Dec. 5, 2006

(54) BORON-DOPED NANOCRYSTALLINE DIAMOND

(75) Inventors: Greg M. Swain, East Lansing, MI (US); Yoshiyuki Show, East Lansing, MI (US); Prerna Sonthalia, East Lansing, MI (US); Malgorzata Witek, Baton Rouge, LA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/991,272

(22) Filed: Nov. 17, 2004

(65) Prior Publication Data

US 2005/0110024 A1   May 26, 2005

Related U.S. Application Data

(60) Provisional application No. 60/524,920, filed on Nov. 25, 2003.

(51) Int. Cl.
*H01L 21/00* (2006.01)

(52) U.S. Cl. .................................... 438/105
(58) Field of Classification Search ................ 438/105
See application file for complete search history.

(56) References Cited

U.S. PATENT DOCUMENTS 6,267,866 B1   7/2001   Glesener et al.

OTHER PUBLICATIONS

Angus, J.C., et al., J. Appl. Phys. 39 2915 (1968).
Hsu, W.L., J. Vac. Sci. Technol. A6 1803 (1988).
Frenklach, M., J. Appl. Phys. 66 395 (1989).
Zhou, D., et al., J. Appl. Phys., 84 1981 (1998).
Jiao, S., et al., J. Appl. Phys. 90 118 (2001).
McCauley, T.G., et al., Appl. Phys. Lett. 73 1646 (1998).
Gruen, D.M., Annu. Rev. Mater. Sci. 29 211 (1999).
Bhattacharyya,S., et al., Appl. Phys. Lett. 79 1 (2001).
Chen, Q., et al., J. Electrochem. Soc. 148 44 (2001).
Fausett, B., et al., Electroanal. 12, 7 (2000).
Keblinski, P., et al., J. Mater. Res. 13, 2077 (1998).
Nemanich, R. J., et al., J. Vac. Sci. Technol. A6, 1783 (1988).
Knight, D. S., et al., J. Mater. Res. 4, 385 (1989).
Bergman, L., et al., J. Appl. Phys., 78, 6709 (1995).
Prawer, S., et al., Chem. Phys. Lett. 332, 93 (2000).
Ferrari, A. C., et al., J. Phys. Rev. 63, 121405 (B2001).
Granger, M. C., et al., Anal. Chim. Acta, 397, 145 (1999).
Granger, M. C., et al., Anal. Chem. 72, 3793 (2000)
Wang, J., et al., New Diamond Front. Carbon Technol. 9, 317 (1999).
Chen, P., et al., Anal. Chem. 68, 3958 (1996).
Granger, M. C., et al., J. Electrochem. Soc. 146, 4551 (1999).
Alehashem, S., et al., Anal. Chem. 67, 2812 (1995).
Pleskov, Y. V., et al., Electrochem. Solid State Lett., 3, 141 (2000).
Qiu, F., et al., Anal. Chem. 72, 2362 (2000).
Engelmann, E. E., et al., Langmuir, 8, 1637 (1992).
Hunt DuVall, S., et al., Anal. Chem. 71, 4594 (1999).
Koppang, M., et al., Anal. Chem. 71, 1188 (1999).
Witek, M. A., et al., Anal. Chim. Acta, 440, 119 (2001).
Vinokur, N., et al., J. Electrochem.Soc. 146, 125 (1999).
Manivannan,A., et al., Electrochem.Solid State Lett. 2, 454 (1999).
Prado, C., et al., Electroanal. 14, 262 (2002).

*Primary Examiner*—Scott B. Geyer
(74) *Attorney, Agent, or Firm*—Ian C. McLeod; Mary M. Moyne; Steven E. Merritt

(57) ABSTRACT

A conductive boron doped nanocrystalline diamond is described. The boron doped diamond has a conductivity which uses the boron in the crystals as a charge carrier. The diamond is particularly useful for electrochemical electrodes in oxidation-reduction reactions and decontamination of aqueous solutions.

5 Claims, 8 Drawing Sheets

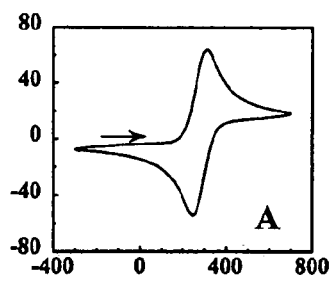
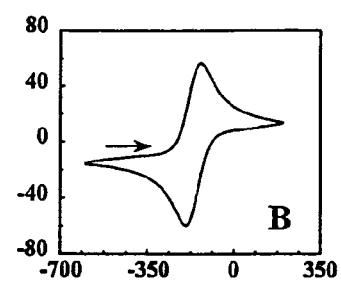
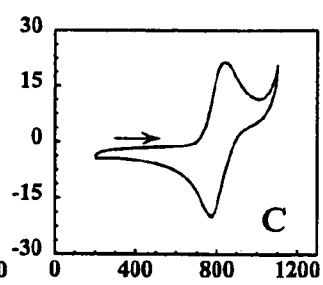
FIG. 6A          FIG. 6B          FIG. 6C
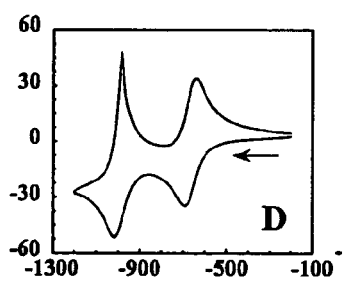
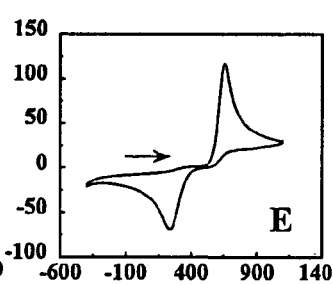
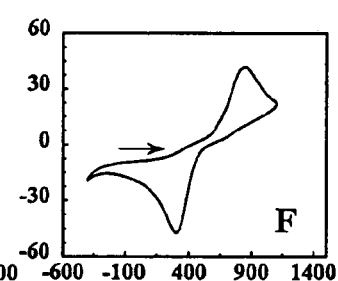
FIG. 6D          FIG. 6E          FIG. 6F

US 7,144,753 B2

BORON-DOPED NANOCRYSTALLINE DIAMOND

CROSS-REFERENCE TO RELATED APPLICATIONS

This application claims priority to Provisional Application Ser. No. 60/524,920, filed Nov. 25, 2003.

STATEMENT REGARDING GOVERNMENT RIGHTS

This invention was supported by grants from the United States Department of Agriculture (No. 2001-35102-100 45) and the National Science Foundation (CHE-0049090). The Government has certain rights in the invention.

STATEMENT REGARDING FEDERALLY SPONSORED RESEARCH OR DEVELOPMENT

Not Applicable

BACKGROUND OF THE INVENTION (1) Field of the Invention

The present invention relates to boron doped nanocrystalline diamond and in particular to electrodes which are electrically conductive. In particular the present invention relates to boron doped diamond wherein exposed surfaces are terminated by carbon-hydrogen or carbon-oxygen bonds.

(2) Description of Related Art

High-quality diamond films can be formed with two different morphologies and microstructures, microcrystalline and nanocrystalline. The distinction between these two structures arises from the nominal grain size, which for microcrystalline films is >1 µm and for nanocrystalline films is ~20 nm, preferably between 1 and 50 nm. Conventional microcrystalline diamond CVD growth uses hydrocarbon-hydrogen (e.g. 1% $CH_4$/99% $H_2$) gas mixtures and it is known under such growth conditions that hydrogen plays a number of critical roles (Gruen, D. M., MRS Bull. 23 32 (1998); Angus, J. C., et al., J. Appl. Phys. 39 2915 (1968); Hsu, W. L., J. Vac. Sci. Technol. A6 1803 (1988); Frenklach, M., J. Appl. Phys. 65 5124 (1989); Butler, J. E., et al., MRS Bull. 23 22 (1998); Zhou, D., et al., J. Appl. Phys., 84 1981 (1998); Jiao, S., et al., J. Appl. Phys. 90 118 (2001)); McCauley, T. G., et al., Appl. Phys. Lett. 73 1646 (1998)). Among these are stabilization of the diamond lattice and removal of $sp^2$-bonded carbon nuclei, when formed, due to preferential gasification over $sp^3$-bonded diamond. Gruen discovered that phase-pure nanocrystalline diamond can be grown from $CH_4$/Ar gas mixtures containing very little or no added hydrogen (Gruen, D. M., MRS Bull. 23 32 (1998); Zhou, D., et al., J. Appl. Phys. B84 1981 (1998); Jiao, S., et al., J. Appl. Phys. 90 118 (2001); McCauley, T. G., et al., Appl. Phys. Lett. 73 1646 (1998); Gruen, D. M., Annu. Rev. Mater. Sci. 29 211 (1999); and Bhattacharyya, S., et al., Appl. Phys. Lett. 79 1 (2001)). There are two kinds of nanocrystalline diamond films often described. The first are films deposited from high $CH_4/H_2$ (>3%) gas mixtures. These films have nanometer-sized features due to the high rate of nucleation, but are generally of low quality (so-called "dirty" diamond) with significant levels of secondary nucleation and $sp^2$-bonded carbon impurity phases. The second are films deposited from $CH_4$/Ar (~1%) gas mixtures. These films consist of randomly oriented, nanometer-sized grains of phase-pure diamond and are generally of higher quality.

The grains are on the order of 20 nm in diameter, and the grain boundaries consist of Π-bonded, carbon atoms (ca. 2–4 atoms wide). The physicochemical properties of the grain boundary change the conductivity and are thus controlled by the grain boundary.

WO 02/31891 A1 describes ultrananocrystalline diamond electrodes containing nitrogen as a dopant. The conductivity is primarily between the grains.

U.S. Pat. No. 6,267,866 to Glesener et al discloses microcrystalline diamond electrodes which are boron doped and deposited on mesh supports. The conductivity is primarily between the grains.

There is a need for improved conductivity in nanocrystalline diamond films.

SUMMARY OF THE INVENTION

The present invention relates to an electrically conductive nanocrystalline diamond containing elemental boron in the crystals as a dopant in a concentration of at least about $10^{19}$ atoms/cm$^3$, an electrical conductivity of at least about $1(\Omega$ cm$)^{-1}$ and wherein the conductivity is brought about by charge carriers introduced by the boron, as opposed to grain boundaries between the crystals. The diamond can be as a film on a substrate. The substrate is preferably a p-type silicon (100). The diamond can be deposited by chemical vapor deposition from methane and argon or a methane, hydrogen and argon gas mixture in the presence of the boron compound. The diamond surface carbon atom can be terminated with hydrogen or oxygen.

In particular, the present invention relates to an electrode having a surface of an electrically conductive nanocrystalline diamond containing elemental boron in the crystals as a dopant in a concentration of at least about $10^{19}$ atoms/cm$^3$, an electrical conductivity of at least about $1(\Omega$ cm$)^{-1}$ and wherein the conductivity is brought about by charge carriers introduced by the boron, as opposed to carriers introduced by pi-bonded carbon in the grain boundaries between the crystallites.

The present invention particularly relates to an improvement in a method for treating an aqueous solution containing an electrically responsive compound, which comprises electrolyzing the compound with the electrode previously described. The compound is preferably oxidized or reduced.

The present invention particularly relates to a process for forming the nanocrystalline diamond as previously described which comprises chemically vapor depositing the diamond on the substrate, from a gaseous mixture of a boron compound, methane, hydrogen and argon, onto a substrate which enables the formation of the nanocrystalline diamond.

The flow rates of $CH_4$, $Ar_2$ and $H_2$ are preferably about 1, 94 and 5 sccm and at a pressure of 140 Torr and at a temperature of 800° C. $B_2H_6$ is preferably added as the boron compound. Preferably after the depositing the diamond is exposed to hydrogen during cooling, wherein alternatively the diamond is exposed to oxygen during cooling.

The deposition, characterization, and electrochemical responsiveness of the preferred boron-doped nanocrystalline diamond thin-film electrodes are described. The films consist of clusters of diamond grains, ~50–100 nm in diameter, and possess an rms surface roughness of 34 nm over a 5×5 µm$^2$ area. The individual and randomly ordered diamond grains are approximately 10–15 nm in diameter, as evidenced by TEM. The ~4-µm-thick films were deposited by microwave-assisted chemical vapor deposition (CVD) using a $CH_4/H_2$/Ar source gas mixture (1%/5%/95%) using $B_2H_6$ as the preferred boron compound. Under these conditions, $C_2$, rather than $CH_3$, appears to be the dominant nucleation and growth precursor.

The nanocrystallinity is a result of a nucleation and growth mechanism discovered by Gruen, which involves the insertion of $C_2$ carbon dimer into C—H bonds on the growth surface (MRS Bull. 23 32 (1998)). The nanocrystalline morphology results from a high renucleation rate. However unlike previously reported nanocrystalline diamond thin films that have electrical properties dominated by the high fraction of Π-bonded carbon atoms in the grain boundaries, the present films are doped with boron, either using $B_2H_6$ or a solid-state boron diffusion source, and the electrical properties appear to be dominated by the charge carriers in the diamond. The films were characterized by scanning-electron microscopy, atomic-force microscopy, transmission-electron microscopy, visible-Raman spectroscopy, x-ray diffraction, boron-nuclear-reaction analysis, and cyclic voltammetry, using $Fe(CN)_6^{3-/4-}$, $Ru(NH_3)_6^{3+/2+}$, $IrCl_6^{2-/3-}$, methyl viologen, $Fe^{3+/2+}$, and 4-tert-butylcatechol. Analytical application of this advanced carbon electrode material for the detection of trace metal ions is discussed.

BRIEF DESCRIPTION DRAWINGS

Figure 4:
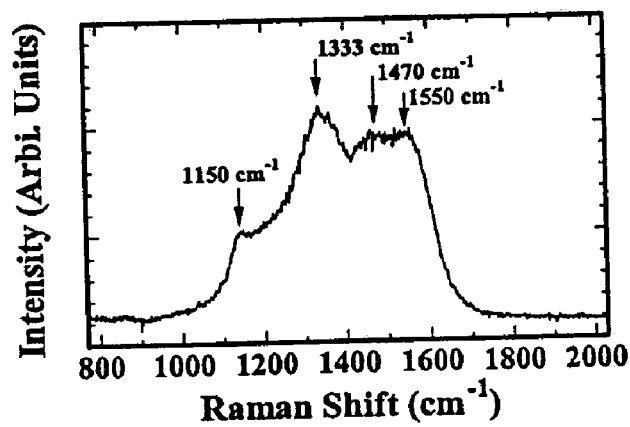

FIG. 4 is a visible Raman spectrum for a boron-doped nanocrystalline diamond thin film according to the present invention. ($\lambda_{ex}$=532 nm. Laser power=50 mW. Integration time=5 s)

Figure 5A:
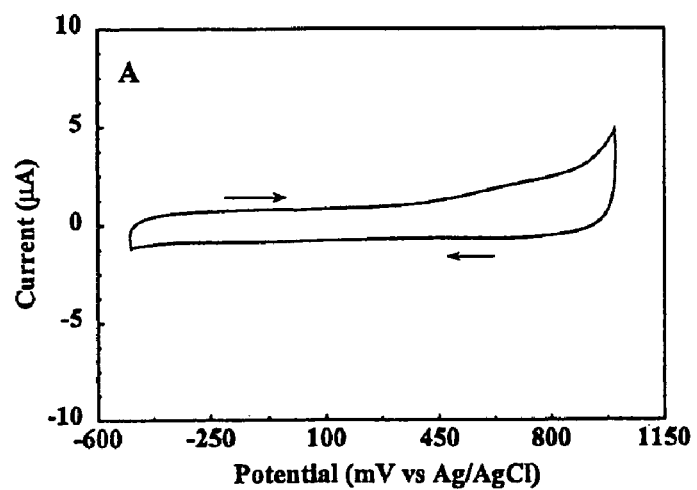
Figure 5B:
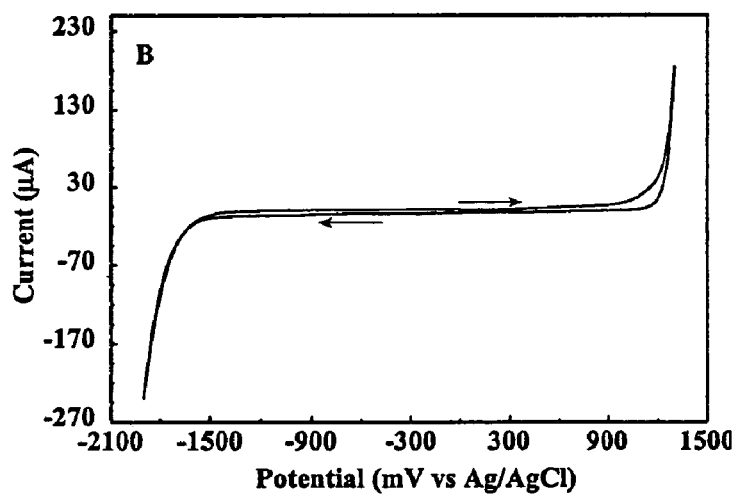

FIGS. 5A and 5B are graphs showing background cyclic voltammetric i-E curves in (A) 1.0 M KCl (narrow potential range) and (B) 1.0 M KCl (working potential window) for a nanocrystalline boron-doped diamond thin film according to the present invention. (Scan rate=100 mV/s. Electrode geometric area=0.2 $cm^2$)

FIGS. 6A to 6F are graphs showing cyclic voltammetric i-E curves for (A) 1.0 mM $Fe(CN)_6^{3-/4-}$, (B) 1.0 mM $Ru(NH_3^{2+/3+})$, (C) 0.25 mM $IrCl_6^{2-/3-}$, (D) 0.50 mM Methyl viologen ($MV^{+2/+}$) in 1 M KCl, (E) 1.0 mM 4-tert-butylcatechol, and (F) 1.0 mM $Fe^{2+/3+}$ in 0.1 M $HClO_4$ for a nanocrystalline boron-doped diamond thin film according to the present invention. (Scan rate=100 mV/s. Electrode geometric area=0.2 $cm^2$)

Figure 7:
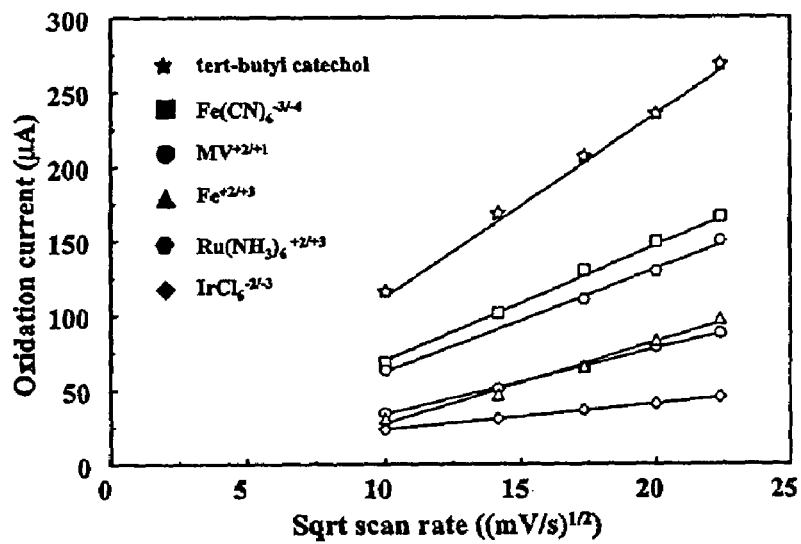

FIG. 7 is a graph showing plots of oxidation current (µA) versus scan $rate^{1/2}$ for $Fe(CN)_6^{3-/4-}$, $Ru(NH_3)_6^{2+/3+}$, $IrCl_6^{2-/3-}$, methyl viologen ($MV^{+2/+}$), 4-tert-butylcatechol, and $Fe^{2+/3+}$ for a nanocrystalline boron-doped diamond thin film according to the present invention.

Figure 8:
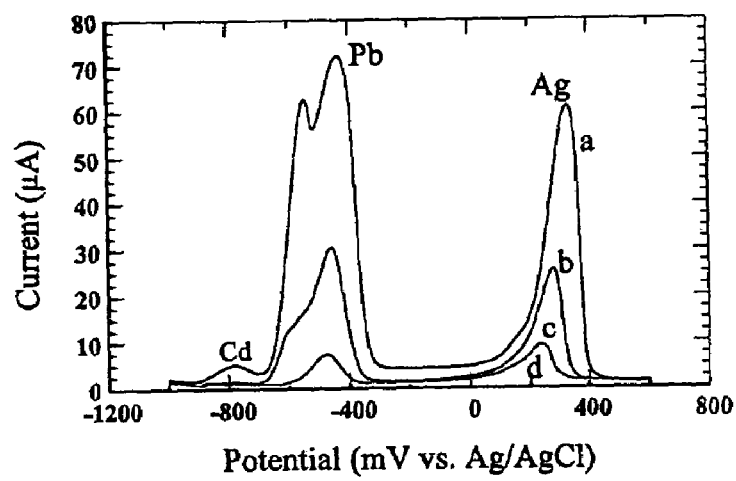

FIG. 8 is a graph showing differential pulse anodic-stripping voltammetric iE curves for Ag(I), Pb(II), and Cd(II) for a boron-doped nanocrystalline diamond thin film in 0.1 M acetate buffer, pH 4.5. The metal ion concentrations are (a) 10, (b) 1, (c) 0.5, (d) 0.1, and (e) 0.01 µM. Preconcentration at −1000 mV for 3 minutes (no stirring) according to the present invention.

Figure 9:
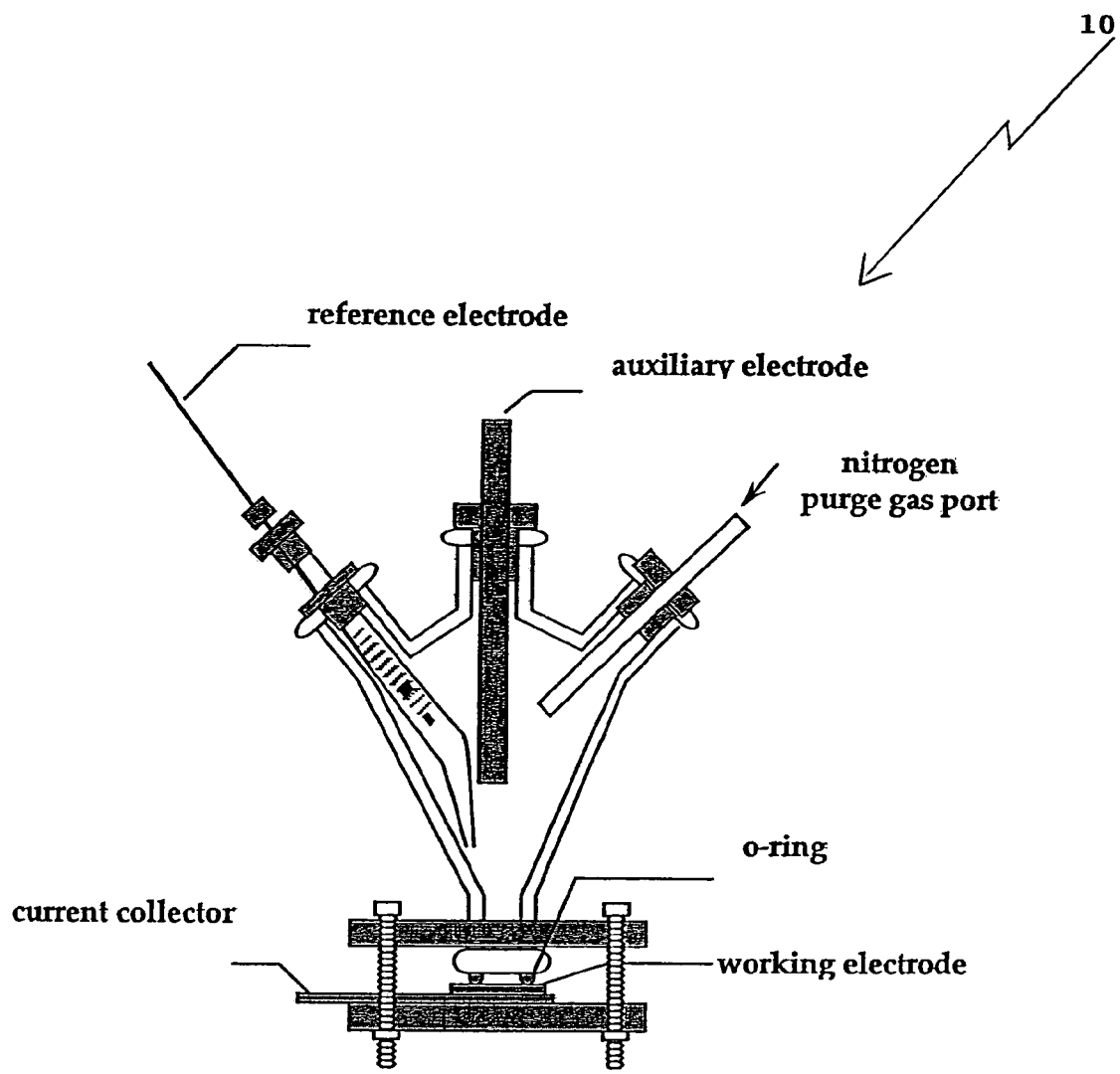

FIG. 9 is a schematic view of the electrolysis cell 10 used to test the nanocrystalline boron doped diamond thin film electrodes of the present invention.

Figure 10A:
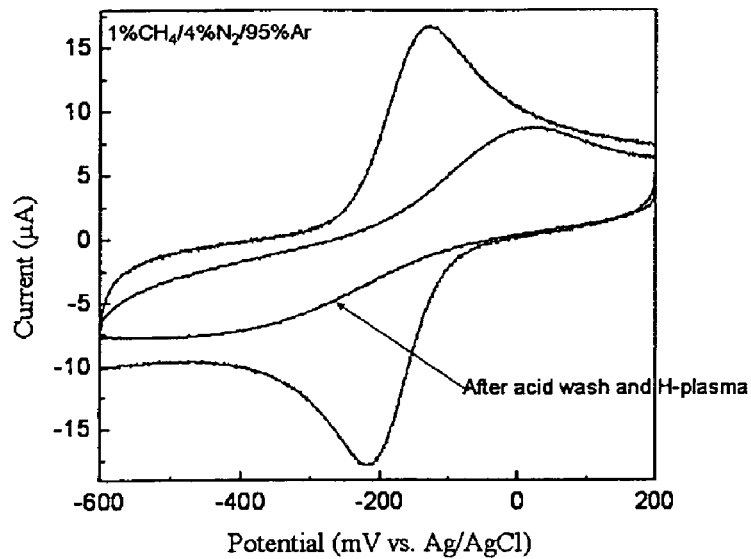
Figure 10B:
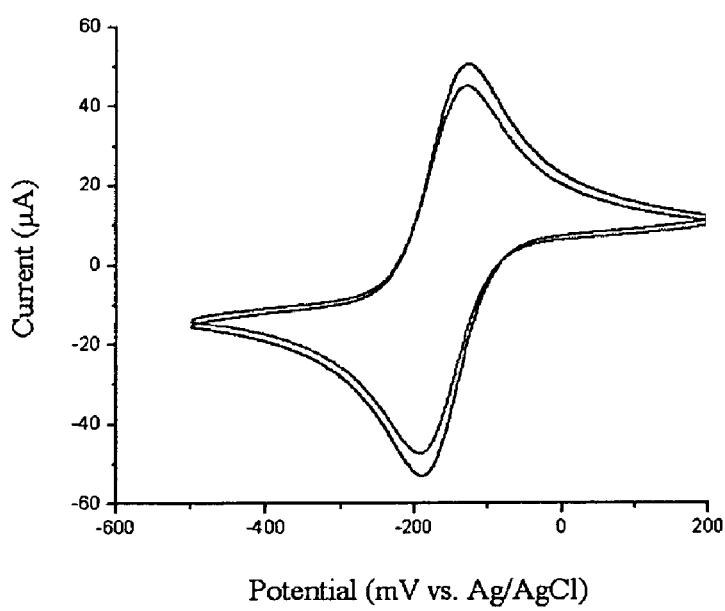

FIGS. 10A and 10B show cyclic voltammetric i-E curves. FIG. 10A is for a prior art diamond film and FIG. 10B is for the films of the present invention.

DESCRIPTION OF PREFERRED EMBODIMENTS

The present invention involves boron-doped, phase pure nanocrystalline diamond thin films. The most remarkable difference in films grown using hydrogen-poor Ar gas mixtures, compared with conventional hydrogen-rich mixtures, is the nanocrystallinity of the former compared with the microcrystallinity of the latter. The nanocrystallinity is a result of a growth and nucleation mechanism involving the insertion of carbon dimer, $C_2$, into surface C—H bonds. The $C_2$ addition is believed to occur by a two-step growth mechanism (McCauley, T. G., et al., Appl. Phys. Lett. 73 1646 (1998)). A $C_2$ molecule approaches the unreconstructed monohydride surface and inserts into a C—H bond. The $C_2$ molecule then rotates to insert its other carbon into a neighboring C—H bond on the surface. A $C_2$ molecule then inserts into an adjacent C—H bond, parallel to the newly inserted $C_2$ dimer. The original state of the surface is recovered by the formation of a bond between carbon atoms in the adjacent surface dimers. Very high rates of heterogeneous nucleation are observed, on the order of $10^{10}$ $cm^{-2}$, and the resulting films consist of randomly oriented, phase-pure diamond grains with well-defined grain boundaries (Guen, D. M. Annu. Rev. Mater. Sci. 29 211 (1999)). The smooth nanocrystalline films possess interesting mechanical, tribological, and electrical properties owing to the small grain size. For example, the films transition from an electrically insulating to an electrically conducting material with a reduction in crystallite size from the micrometer to the nanometer level (Bhattacharyya, S., et al., Appl. Phys. Lett. 79 1 (2001)). This is largely due to the presence of high-energy, high-angle grain boundaries that contain Π-bonded carbon atoms (i.e. a high density of electronic states over a wide energy or potential range). The grain boundaries are conducting because of Π-states, and since their numbers vastly increase with decreasing crystallite size, the entire film becomes electrically conducting and functions as an electrode material (Chen, Q., et al., J. Electrochem. Soc. 148 44 (2001)). Theoretical calculations suggest that localized electronic states are introduced into the band gap of these films due to, the presence of $sp^2$-bonded dimers and $sp^3$-hybridized dangling bonds in the grain boundaries (Gruen D. M., Annu. Rev. Mater. Sci. 29 211 (1999)). There is a lack of spatial connectivity among the $sp^2$-bonded carbon sites; therefore, the associated gap states do not form an extended Π-system, but rather are localized.

We recently reported on the structural and electrochemical characterization of nitrogen-incorporated nanocrystalline diamond thin-film electrodes, deposited from $CH_4/N_2$/Ar gas mixtures (Chen, Q., et al., J. Electrochem. Soc. 148 44 (2001)). The electrical conductivity of these nitrogen-containing films increases with increasing nitrogen content up to about 5%, and the films are generally more conductive than the early forms of nanocrystalline diamond (Chen, Q., et al., J. Electrochem. Soc., 148, 44 (2001: and Fausett, B., et al., Electroanal. 12, 7 (2000)). Recent Hall Effect measurements (mobility and carrier concentration) for films deposited with 10 and 20% $N_2$ revealed carrier concentrations of $2.0 \times 10^{19}$ and $1.5 \times 10^{20}$ $cm^{-3}$, respectively (Bhattacharyya, S., et al., Appl. Phys. Lett. 79, 1 (2001)). The room-temperature carrier mobilities were 5 and 10 $cm^2/V \cdot s$, respectively. A negative Hall coefficient indicated that electrons are the majority charge carrier. An explanation for the effect of nitrogen is that the impurity causes microstructural changes within the grain boundaries (i.e., increased Π-bonding), resulting in an increase in the localized density of electronic states. Computations indicate that the incorporation of nitrogen into the grain boundaries is energetically favored by 3–5 eV over substitutional insertion into the grains (Gruen, D. M., *Annu. Rev. Mater. Sci.* 29, 211 (1999)).

The electrical properties of the nitrogen-containing nanocrystalline diamond films are largely influenced by the Π-bonding in the grain boundaries (Gruen, D. M., *Annu. Rev. Mater. Sci.* 29, 211 (1999); Ghattacharyya, S., et al., *Appl. Phys. Lett.* 79, 1 (2001); Chen, Q., et al., *J. Electrochem. Soc.* 148, 44 (2001); Fausett, B., et al., *Electroanal.*, 12, 7, (2000); and Keblinski, P., et al., *J. Mater. Res.* 13, 2077 (1998). While these electrode materials possess good electrochemical behavior, much like those for high-quality microcrystalline diamond films, their electrical response is strongly linked to the physicochemical properties of the grain boundaries. Therefore, the electrochemical response can be strongly influenced by changes in the Π-bonded grain boundary atoms. This is particularly true during exposure to chemically harsh solutions that can cause the oxidative etching or disruption of the Π-bonded grain boundary atoms. It would be better if the nanocrystalline diamond films exhibited a through-grain conduction mechanism as a result of impurity incorporation, such as boron doping. Such films should exhibit electrical conductivity that scales with the doping level and should have electrochemical properties that are largely unaffected by changes in the physicochemical properties of grain boundaries.

We report on the characterization and electrochemical responsiveness of boron-doped nanocrystalline diamond thin-film electrodes. The boron doping imparts electrical conductivity to the entire film (i.e., through-grain conduction); hence, the electrical conductivity is no longer dominated by the grain boundaries. The films were deposited form a 1% $CH_4$/5% $H_2$/94% Ar source gas mixture using 800 W of microwave power and a system pressure of 140 Torr. The continuous films were deposited for 2 h with a film thickness of about 4 μm and an apparent in-plane electrical resistivity of 0.2 Ω-cm. The films were characterized by scanning electron microscopy (SEM), atomic force microscopy (AFM), transmission electron microscopy (TEM), X-ray diffraction (XRD), visible-Raman spectroscopy, and cyclic voltammetry, using $Fe(CN)_6^{3-/4-}$, $Ru(NH_3)_6^{+3/+2}$, $IrCl_6^{3-/4-}$, methyl viologen, $Fe^{3+/2+}$, and 4-tert-butylcatechol. Electroanalytical application of the electrodes for the determination of metal ions, $Cd^{2+}$, $Pb^{2+}$, and $Ag^+$, via anodic stripping voltammetry is discussed. The results indicate that (i) highly conducting nanocrystalline diamond thin films can be deposited in a short period of time (i.e., cost savings), (ii) the phase-pure, smooth films consist of ~20-nm diamond grains, (iii) the films have electrical conductivity that scales with the boron-doping level and is largely independent of the physicochemical properties of the grain boundaries, and (iv) the films possess electrochemical properties similar to those observed for high-quality, hydrogen-terminated, microcrystalline diamond thin films.

Experimental Section

Electrode Fabrication. The boron-doped nanocrystalline diamond thin films were deposited on p-type Si(100) substrates (~$10^{-3}$ Ω-cm, Virginia Semiconductor Inc., Fredricksburg, Va.) using a commercial microwave-assisted, chemical vapor deposition (CVD) system (1.5 kW, ASTeX Inc., Lowell, Mass.). The surface of the Si substrate was mechanically scratched on a felt polishing pad with 1-μm-diameter diamond powder (GE Superabrasives, Worthington, Ohio). The scratched substrate was then sequentially washed with ultrapure water, isopropyl alcohol (IPA), acetone, IPA, and ultrapure water to remove polishing debris from the scratches. This is a critical step in the pretreatment. The cleaned substrate was then placed in the CVD reactor on a molybdenum substrate holder. The scratching treatment enhances the nucleation of small diamond particles during the initial growth stage. This leads to the formation of a thin and continuous nanocrystalline diamond film in a relatively short period of time. Ultrahigh purity $CH_4$, Ar, and $H_2$ (99.999%) were used as the source gases. The gas flow rates were 1, 94, and 5 sccm, respectively. The microwave power and system pressure were maintained at 800 W and 140 Torr, respectively. The substrate temperature was estimated, by an optical pyrometer, to be about 800° C. The deposition time was 2 h and the resulting nanocrystalline diamond thin film was approximately 4-μm-thick, as estimated from the weight change.

Boron doping of the nanocrystalline diamond was accomplished using either a solid-state or gas-phase boron source. A BoronPlus (GS 126, Techneglas, Inc., Perrysburg, Ohio) solid-state ceramic source was placed under the Si substrate on the molybdenum stage. Boron diffuses from the ceramic matrix as $B_2O_3$ and is incorporated into the film during growth. On the other hand, $B_2H_6$, diluted in $H_2$, was used as a gas-phase source and was introduced into the source gas mixture. The concentration of $B_2H_6$ can be varied preferably between about 1 and 20 ppm, but was fixed at 10 ppm in the Examples.

The plasma was ignited and the growth was initiated with all gases flowing into the reactor. At the end of the deposition period, the $CH_4$ flow was stopped and the Ar and $H_2$ continued. The diamond film remained exposed to the $H_2$/Ar plasma for approximately 10 min at the deposition conditions. The Ar flow was then stopped and the substrate was cooled in an $H_2$ plasma (i.e., atomic hydrogen) to an estimated temperature of <400° C. by slowly reducing the power and pressure over a 4-min period. Post growth annealing in atomic hydrogen is essential for etching away adventitious nondiamond carbon impurity, minimizing dangling bonds, and ensuring full hydrogen termination.

Material Characterization. The surface morphology of the boron-doped nanocrystalline diamond thin films was investigated using scanning electron microscopy (SEM) (Hitachi, S-4500, Japan), atomic force microscopy (Nanoscope IIIa, Digital Instruments/Veeco Metrology Group, Santa Barbara, Calif.), and transmission electron microscopy (TEM) (JEM-4000EX, JEOL, Japan). The sample for the TEM investigations was prepared by growing a thin nanocrystalline diamond film for 10 min on a Si substrate and dissolving the substrate using an $HF/HNO_3$ solution. The free-standing pieces of diamond were then collected from solution on a copper TEM grid. The bulk crystallinity and microstructure were characterized by x-ray diffraction (1.540 Å, X-pert MRD, Philips, Netherlands), and visible-Raman spectroscopy (Raman 2000, Chromex Inc., Albuquerque, N. Mex.), respectively. The 2θ XRD measurements were performed from 30 to 100°. The Raman spectrograph consisted of a diode-pumped, frequency-doubled Nd:YAG laser (532-nm excitation at 50 mW), a multichannel detector, and a focusing microscope with a 20× objective lens. The boron dopant concentration was determined by boron nuclear-reaction analysis (Surface Characterization Facility, Case Western Reserve University). Calibration was performed with a piece of high-quality boron nitride. The carrier concentration was determined through a Hall measurement (Model HL 5500, Bio-Rad Microscience, England) performed at room temperature under a magnetic field of 0.492 T. A square van der Pauw arrangement using Ti contacts was employed. Water contact angles (First Ten Angstroms, Portsmouth, Va.) of ca. 80° were measured and were stable with time, indicative of a hydrophobic surface.

Electrochemistry. Most of the electrochemical measurements were made with a CYSY-2000 computerized potentiostat (Cypress System Inc., Lawrence, Kans.) using a single-compartment, three-electrode glass cell, as shown in FIG. 9. The diamond working electrode was pressed against a Viton O-ring and clamped to the bottom of the cell. Ohmic contact was made with an aluminum plate after placing a bead of In/Ga alloy on the backside of the scratched and cleaned substrate. A graphite rod was used as the counter electrode and a commercial Ag/AgCl electrode (3 M KCl) served as the reference ($E°_{Ag/AgCl}=-0.045$ V vs SCE). The geometric area of the working electrode was ca. 0.2 cm$^2$. All measurements were performed at room temperature, ~25° C. The supporting electrolytes were 1.0 M KCl and 0.1 M HClO$_4$. The concentrations of Fe(CN)$_6^{3-/4-}$, Ru(NH$_3$)$_6^{2+/3+}$, 4-tert-butylcatechol, and Fe$^{2+/3+}$ were 1.0 mM, IrCl$_6^{2-/3-}$ was 0.25 mM, and methyl viblogen was 0.5 mM.

The differential pulse voltammetry for the trace metal ion analysis was performed on a Model 650A computerized potentiostat (CH Instruments, Austin, Tex.). All measurements were made in solutions deoxygenated with N$_2$ for at least 10 minutes initially and then for 2 minutes after each anodic stripping sweep. The solutions were blanketed with the gas during all measurements and the electrochemical cell placed inside an electrically grounded Faraday cage. The electrolyte solution was 0.1 M acetate buffer, pH 4.5. The commercial reference electrode was isolated from the main electrolyte solution, using a cracked-glass tube (i.e., double junction). The tube was filled with the acetate buffer solution. The anodic-stripping voltammetric measurements used a 3-min deposition time with no stirring and a 0.5-min "quiet" time prior to initiation of the anodic sweep. The differential pulse voltammetry settings were as follows: 100-mV pulse height; 2-mV step height; 50-ms pulse width; 35-ms sampling time; and a constant potential of 600 mV for 120 s after completion of the anodic sweep to fully oxidize all metal deposits.

Chemicals. All solutions were prepared with ultrapure water (>1.7 MΩ) from an E-pure purification system (Barnstead). The KCl, NaCl, K$_4$Fe(CN)$_6$, Cl$_3$Ru(NH$_3$)$_6$, K$_2$IrCl$_6$, 1,1'-dimethyl-4,4'-bipyridinum dichloride(methyl viologen), and 4-tert-butylcatechol (Aldrich Chemical), Fe$_2$(SO$_4$)$_3$.6H$_2$O (Matheson Coleman & Bell), HClO$_4$ (ultrapure, Aldrich Chemical), and sodium hydroxide (Fisher Scientific) were reagent-grade quality, used as received. Silver nitrate (Fisher), cadmium nitrate (Aldrich), cupric nitrate (Aldrich), lead nitrate (Aldrich), and zinc nitrate (Aldrich) were all reagent-grade quality, used without additional purification. Acetate buffer (0.1 M) was prepared by mixing appropriate amounts of 99% sodium acetate (Aldrich) and acetic acid (Aldrich). All solutions were prepared fresh daily and purged with N$_2$ (99.999%) for 10 min prior to any electrochemical measurement. All glassware was cleaned by a three-step procedure: ethanol/KOH bath, alconox/ultrapure water solution, and ultrapure water rinse.

Safety: B$_2$H$_6$ (0.1% diluted in hydrogen) is a hazardous gas that should be appropriately contained within a vented gas cabinet. All other reagents and chemicals can be used with routine safety precautions.

Results and Discussion

Figure 1:
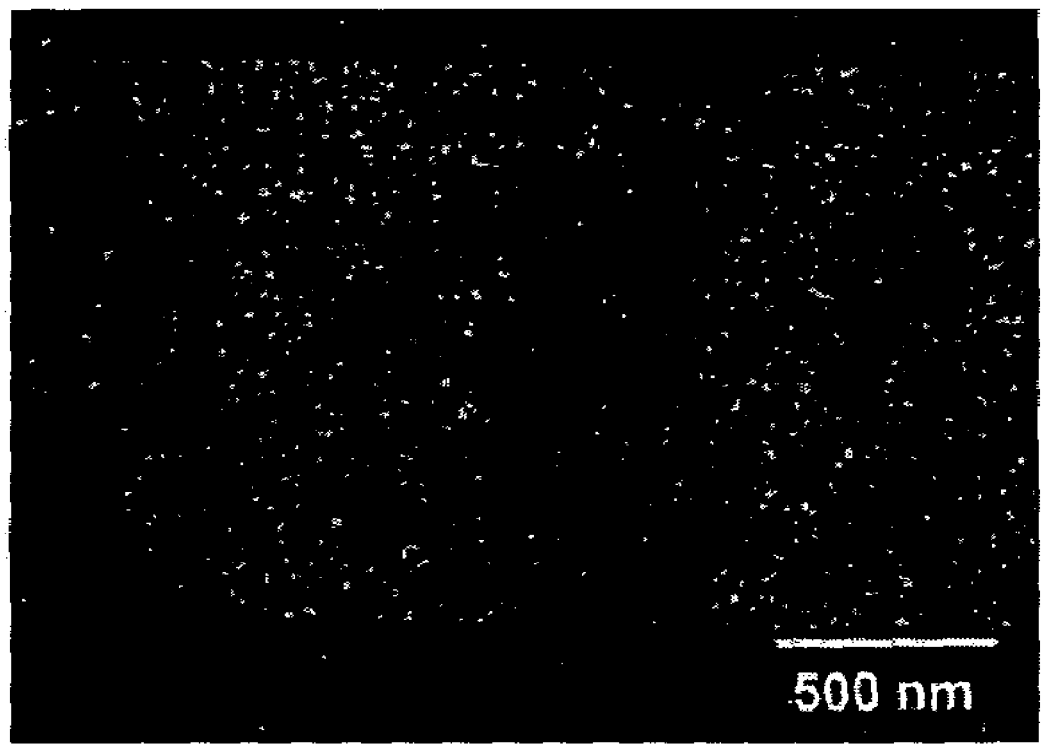
FIG. 1 is a SEM image of a boron doped diamond thin film according to the present invention.

Material Characterization. FIG. 1 shows a top-view SEM image of a boron-doped nanocrystalline diamond thin film deposited for 2 h. The smooth and uniformly coated film is composed of nodular features ~50–100 nm in diameter. No voids or cracks were found in the coating and the thickness was uniform over the entire substrate. AFM images were also acquired to probe the film morphology. The root-mean-square surface roughness was found to be 34 nm over a 5×5 μm$^2$ area and was independent of the growth time (i.e., film thickness). The nodular features are actually clusters of individual diamond grains formed as a result of the high nucleation rate.

Figure 2A:
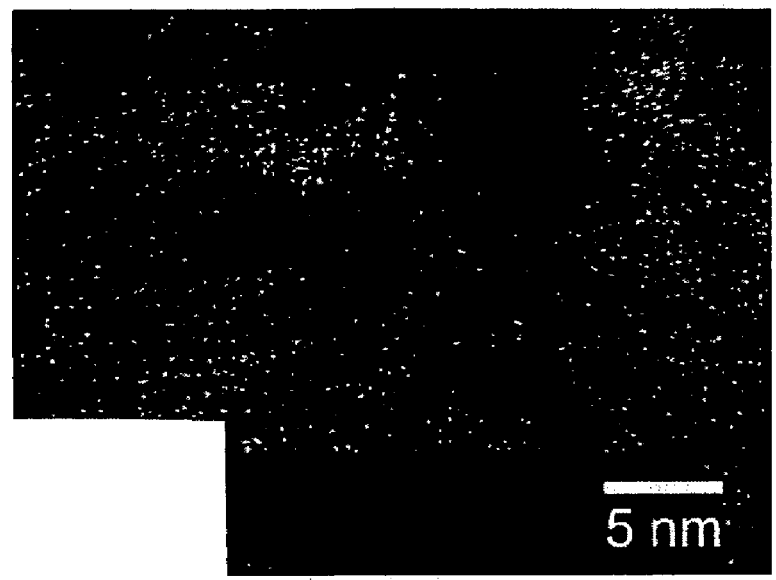
FIG. 2A is a TEM image and FIG. 2B is a TED pattern for a boron doped nanocrystalline diamond thin film according to the present invention.
Figure 2B:
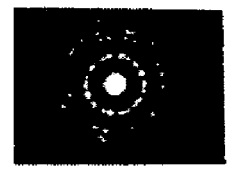

FIG. 2A shows a TEM image for the film, which is representative of several that were taken. The film consists of diamond grains with diameters from 10 to 16 nm. Aggregates of these diamond grains form the nodular features seen in FIG. 1. Moreover each diamond grain is a single crystal and randomly oriented in the film. This conclusion is based on the appearance of the lattice-fringe patterns and their orientational differences from grain-to-grain. A rough estimate of the fringe spacing was made, even through these are not high-resolution images. The estimated spacing on at least a couple of grains is ~0.20 nm. This is close to the 0.206-nm interplanar distance expected for diamond {111} planes. The transmission-electron diffraction (TED) pattern from one of the grains, shown in FIG. 2B, shows an intense spotted-ring pattern, indicative of atomically ordered but randomly oriented grains. The diffraction pattern is indexed to the (111), (022), (113), (004), (133), (224), (15), and (333) planes of cubic diamond (ASTM 6-0675).

Figure 3:
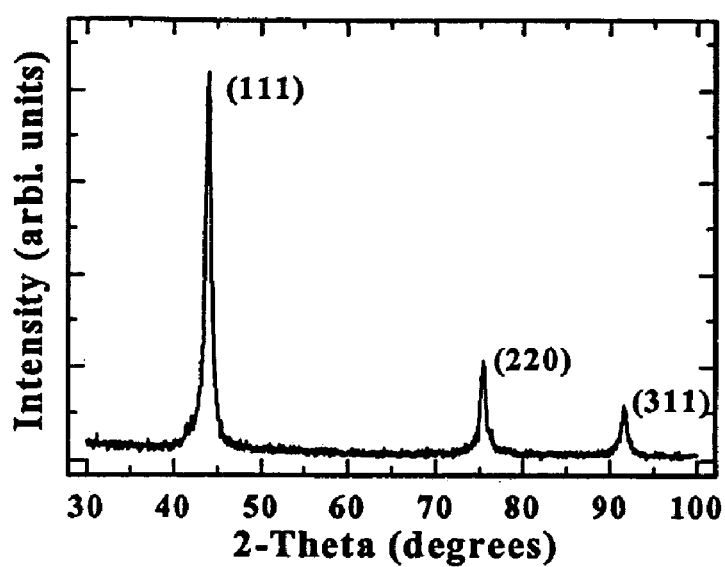
FIG. 3 is an X-ray diffraction pattern for a boron doped diamond thin film according to the present invention.

FIG. 3 shows an XRD spectrum for the film. Three broad reflections are observed at 2θ values of 43.8, 75.5, and 91.5°. These reflections are assigned to the (111), (220), and (311) planes of the cubic diamond, respectively. The peaks are broader than they are for a microcrystalline film of the same approximate thickness due to the 2 orders of magnitude, or more, smaller diamond grain size in the nanocrystalline film. Table 1 summarizes the calculated lattice spacings and the relative peak intensities. Reference data for cubic diamond powder (ASTM or PDF 6-0675) are also presented, for comparison. The diffraction data reveal that the bulk structure is sp$^3$-bonded diamond.

TABLE 1

XRD Peak Intensities and Calculated Lattice Spacings for a Boron-Doped Nanocrystalline Diamond Thin Film

| | Measured | | | | ASTM (6–0675) | |
| --- | --- | --- | --- | --- | --- | --- |
| | diffraction | | | | | |
| Plane | angle (deg) | fwhm (deg) | spacing (Å) | relative intensity | spacing (Å) | relative intensity |
| (111) | 44 | 0.75 | 2.06 | 100 | 2.06 | 100 |
| (220) | 75.5 | 0.65 | 1.26 | 23 | 1.26 | 25 |
| (311) | 91.5 | 1.0 | 1.07 | 13 | 1.07 | 16 |

FIG. 4 shows a visible-Raman spectrum for the film. This spectrum is characteristic of high-quality nanocrystalline diamond films. A single, sharp peak at 1332 cm$^{-1}$ in the Raman spectrum is frequently used as a signature of high-quality, single-crystal, or large-grained diamond (Keblinski, P., et al., *J. Mater. Res.* 13, 2077 (1998); and Nemanich, R. J., et al., *J. Vac. Sci. Technol.* A6, 1783 (1988)). The spectrum for the nanocrystalline film is quite different.

Broad peaks are seen at 1150, 1333, 1470, and 1550 cm$^{-1}$. The peak at 1333 cm$^{-1}$, atop a large background signal, is associated with the first-order phonon mode of sp$^3$-bonded diamond. Due to resonance effects, the Raman cross-section scattering coefficient (visible excitation) for sp$^2$-bonded carbon is larger (50×) than that for the sp$^3$-bonded carbon, and the scattering intensity for the former can often greatly exceed that for the latter (Knight, D. S., et al., *J. Mater. Res.* 4, 385 (1989)); The peak width (fwhm) for the diamond line is much broader than that for microcrystalline diamond, 140 versus 10 cm$^{-1}$. This is because of the small grain size in the nanocrystalline film. There are two possible causes for the line broadening. One possibility is the well-established confinement model (Bergman, L., et al., *J. Appl. Phys.*, 78, 6709 (1995)). This model states that the smaller the domain size, the larger the range of phonon modes (with different q vector and energy) that are allowed to participate in the Raman process. Hence, the line width results from the spread in phonon energy. Another, and more likely, explanation is phonon scattering by impurities and defects (i.e., grain boundaries) (Bergman, L., et al., *J. Appl. Phys.*, 78, 6709 (1995)). The scattering event shortens the lifetime of the phonons and thus broadens the Raman line.

The peak at 1150 cm$^{-1}$ is often used as a signature for high-quality nanocrystalline diamond (Nemanich, R. J., et al., *J. Vac. Sci. Technol.* A6, 1783 (1988)). Prawer and co-workers, through the study of clean nanocrystalline diamond particles (~5-nm diameter), have attributed this peak to a surface phonon mode of diamond (Prawer, S., et al., *Chem. Phys. Lett.* 332, 93 (2000)). On the other hand, Ferrari and Robertson have made arguments for this peak being associated with sp$^2$-bonded carbon, specifically transpolyacetelylene segments at grain boundaries (Ferrari, A. C., et al., *J. Phys. Rev.* 63, 121405 (B2001)). Their assignment of sp$^2$-rather than sp$^3$-bonded carbon, as has often been proposed, (Nemanich, R. J., et al., *J. Vac. Sci. Technol.* A6, 1783 (1988)) is based on the observations that the peak position changes with excitation energy, the peak intensity decreases with increasing excitation energy, and the peak is always accompanied by another peak at ~1450 cm$^{-1}$, which behaves similarly with excitation energy. We, therefore, tentatively assign the peaks at 1470 and 1550 cm$^{-1}$ to disordered sp$^2$-bonded carbon that is amorphous and is mixed with sp$^3$-bonded carbon. It is important to note that, very likely, the sp$^2$-bonded carbon is confined to the grain boundaries of the nanocrystalline film, producing a network of 3- and 4-fold coordinated carbon atoms (Gruen, D. M., et al., *J. Appl. Phys. Lett.* 68, 1640 (1996)). Additional research is needed to confirm the origins of the 1150- and 1470-cm$^{-1}$ bands.

The boron concentration in the film deposited with 10 ppm B$_2$H$_6$ was determined to be 810 ppm (1.43×10$^{20}$ B/cm$^3$ by boron nuclear-reaction analysis). Preliminary Hall measurements indicated the major carrier to be the hole (positive Hall coefficient), and the carrier concentration and conductivity to be 6.4×10$^{17}$ cm$^{-3}$, a number that seems low, and 10 $\Omega^{-1}$cm$^{-1}$, respectively. The carrier mobility was found to be 90.4 cm$^{-2}$/V·s. More work is required to accurately determine the carrier concentration, mobility, and carrier activation energy.

Electrochemical Responsiveness. FIG. 5A shows a background cyclic voltammetric i-E curve for a boron-doped nanocrystalline diamond thin film in 1.0 M KCl. The curve is largely featureless over the potential range and is stable with cycling. There are no obvious peaks present, associated with redox-active surface carbon-oxygen functionalities, although there is a small anodic charge passed between 500 and 800 mV, just prior to the onset of chlorine evolution (Granger, M. C., et al., *Anal. Chim. Acta*, 397, 145 (1999); and Granger, M. C., et al., *Anal. Chem.* 72, 3793 (2000)). The curve shape is similar to that for boron-doped microcrystalline diamond; however, the current magnitude of the former is slightly higher. For instance, at 250 mV, the anodic current for the nanocrystalline film is 0.96 μA (4.8 μA/cm$^2$), whereas the current for the microcrystalline films is about a factor of 1.5 less at 0.6 μA (3.0 μA/cm$^2$). The higher current may be due to surface faradaic processes because of the increased fraction of exposed Π-bonded carbon in the grain boundaries. This carbon is a source of Π states that contribute to the density of electronic states in the material, increasing the capacitive component of the background current. Some of the sp$^2$-bonded carbon could also be electrochemically active at the potentials probed, giving rise to a faradaic component in the background current. In fact, the background voltammetric currents for both diamond electrodes are too high to be solely due to electric double-layer charging (~10 μF/cm$^2$). From the currents, one calculates apparent double-layer capacitances of 48 and 30 μF/cm$^2$ for the nanocrystalline and microcrystalline films, respectively. The higher apparent capacitance is due, in part, to a low estimate of the electrode area. All currents are normalized to the geometric area of the films. However, both film types have roughness factors >1. Also, as mentioned above, some of the background current is likely due to surface faradaic processes (i.e., oxidation of the carbon in the grain boundaries and in the grains). Importantly, the current for both diamond electrodes is significantly less than that for freshly polished glassy carbon, 7–10 μA (35–50 μA/cm$^2$). The low background current is a characteristic feature of diamond electrodes and leads to improved SBR in electroanalytical measurements (Granger, M. C., et al., *Anal. Chim. Acta* 397, 145 (1999); and Granger, M. C., et al., *Anal. Chem.* 72, 3793 (2000)).

FIG. 5B shows a background cyclic voltammetric i-E curve for the same boron-doped nanocrystalline diamond in 1.0 M KCl over a much wider potential range. The working potential window is about 3.1 V (±100 μA or 500 μA/cm$^2$) with a largely featureless response between the potential limits. The anodic current at 1200 mV is due to the oxidation of chloride to chlorine. The cathodic current flowing at −1800 mV is due to the reduction of water to hydrogen. There is a current crossover at about −1700 mV, indicative of an activation overpotential necessary for the initiation of the hydrogen-evolution reaction. This feature is often observed for diamond films; however, the mechanistic cause of this overpotential is currently unknown. A low background current and wide working potential window (3–3.5 V) are characteristic features of both high quality, nitrogen-incorporated nanocrystalline and boron-doped microcrystalline diamond (Chen, Q., et al., *J. Electrochem. Soc.*, 148, 44 (2001); Granger, M. C., et al., *Anal. Chim. Acta*, 397, 145 (1999); and Granger, M. C., et al., *Anal. Chem.* 72, 3793 (2000)). The background cyclic voltammetric data presented in FIG. 5A,B are very similar to what has been reported for high-quality and well-characterized microcrystalline and ultra-nanocrystalline diamond (Fausett, B., et al., *Electroanal.* 12, 7, (2000); Granger, M. C., et al., *Anal. Chim. Acta*, 397, 145 (1999); and Granger, M. C., et al., *Anal. Chem.* 72, 3793 (2000); and Wang, J., et al., *New Diamond Front. Carbon Technol.* 9, 317 (1999)).

The electrochemical responsiveness of the boron-doped nanocrystalline diamond toward six redox systems was investigated using cyclic voltammetry. The influence of diamond's physical, chemical, and electronic properties on the electrode reaction kinetics and mechanism for these systems has previously been discussed (Granger, M. C., et al., *Anal. Chem.* 72, 3793 (2000)). FIG. 6 shows cyclic voltammetric i-E curves for (A) $Fe(CN)_6^{3-/4-}$, (B) $Ru(NH_3)_6^{2+/3+}$, (C) $IrCl_6^{2-/3-}$, (D) methyl violgen ($MV^{+2/+}$) in 1 M KCl, (E) 4-tert-butylcatechol, and (F) $Fe^{3+/2+}$ in 0.1 M $HClO_4$. The potential scan rate (v) was 0.1 V/s. The $E_{1/2}$ for these redox systems ranges from approximately +800 to −1100 mV, so they are very useful for probing the film's electronic properties over a wide potential range. A summary of some of the cyclic voltammetric data is provided in Table 2.

TABLE 2

Summary of Cyclic Voltammetric Data for a Boron-Doped Nanocrystalline Diamond thin-film Electrode

| Analyte | $\Delta E_p$ (mV) | $Ep^{ox}$ (mV) | $Ip^{ox}$ (μA) | $Ip^{ox}/Ip^{red}$ |
|---|---|---|---|---|
| 0.5 mM $MV^{2+/+}$/1 M KCl | 60 | −633 | 34.5 | 1.1 |
| 1 mM $Ru(NH_3)_6^{3+/2+}$/M KCl | 59 | −135 | 62.7 | 0.99 |
| 1 mM $Fe(CN)_6^{3-/4-}$/M KCl | 63 | 309 | 69.4 | 1.02 |
| 1 mM tert-butylcatechol/0.1 M $HClO_4$ | 419 | 655 | 112.2 | 1.8 |
| 0.5 mM $IrCl_6^{2-/3-}$/1 M KCl | 61 | 823 | 22.7 | 0.98 |
| 1 mM $Fe^{2+/3+}$/0.1 M $HClO_4$ | 679 | 926 | 36.0 | 0.91 |
| 1 mM cadaverine/0.01 M BBpH10.6 | irreversible | 927 | 136.0 | irreversible |

A reversible response is observed for $Fe(CN)_6^{3-/4-}$ with a $\Delta E_p$ of 63 mV and an $i_p^{ox}/i_p^{red}$ of 1.0 $Fe(CN)_6^{3-/4-}$ is a surface-sensitive redox system on both glassy carbon and boron-doped microcrystalline diamond (Granger, M. C., et al., *Anal. Chem.*, 72, 3793 (2000); Wang, J., et al., *New Diamond Front. Carbon Technol.* 9, 317 (1999); and Chen, P., et al., *Anal. Chem.* 68, 3958 (1996)). The electrode reaction kinetics for this couple are strongly influenced by the amount of exposed edge plane on $sp^2$-bonded carbon, as well as the surface cleanliness (Chen, P., et al., *Anal. Chem.* 68, 3958 (1996)). Granger et al. showed that surface carbon-oxygen functionalities on microcrystalline diamond significantly influence $\Delta E_p$ with increasing oxygen content, causing an increase in the peak potential separation (Granger, M. C., et al., *J. Electrochem. Soc.* 146, 4551 (1999)). A similar effect was also observed by Fujishima and co-workers (Yagi, I., et al., *J. Electroanal. Chem.* 173, 473 (1999)). The inhibiting effect of the surface oxygen is reversed if the film is rehydrogenated in a hydrogen plasma (Granger, M. C., et al., *J. Electrochem. Soc.*, 146, 4551 (1999)). Apparently, the oxygen blocks a surface site that is involved in the reaction on the hydrogen-terminated surface. The small $\Delta E_p$ seen for the boron-doped nanocrystalline diamond film is indicative of a high level of surface cleanliness and low surface oxide coverage. In other words, this result suggests the diamond surface is largely hydrogenated and clean surface sites exist for this reaction (Granger, M. C., et al., *J. Electrochem. Soc.* 146, 4551 (1999)).

A reversible response is seen for $Ru(NH_3)_6^{3+/2+}$ with a $\Delta E_p$ of 60 mV and an $i_p^{ox}/i_p^{red}$ of 0.99. A reversible response is also seen for $IrCl_6^{2-/3-}$ with a $\Delta E_p$ of 61 mV and an $i_p^{ox}/i_p^{red}$ of 0.98. The electrode-reaction kinetics for both of these systems are relatively insensitive to the physicochemical properties of both $sp^2$-bonded carbon and diamond electrodes (Granger, M. C., et al., *Anal. Chem.* 72, 3793 (2000); Wang, J., et al., *New Diamond Front. Carbon Technol.* 9, 317 (1999); and Chen, P., et al., *Anal. Chem.* 68, 3958 (1996)). The kinetics are mainly influenced by the density of electronic states at the formal potentials for the couples. In other words, the nanocrystalline diamond electrode possesses a sufficient charge-carrier density at about −200 mV, a potential well negative of the apparent flatband potential (ca. 500 mV vs Ag/AgCl) for a hydrogen-terminated p-type (semiconducting) diamond, and 800 mV, a value positive of the flatband potential (Alehashem, S., et al., *Anal. Chem.* 67, 2812 (1995); Fujishima, A., et al., *Proc. Electrochem. Soc.*, 99–32, 383 (2000); and Pleskov, Y. V., et al., *Electrochem. Solid State Lett.*, 3, 141 (2000)).

A reversible response is seen for $MV^{+2/+}$ with a $\Delta E_p$ of 60 mV and an $i_p^{ox}/i_p^{red}$ of 1.1. Like $Ru(NH_3)_6^{2+/3+}$ and $IrCl_6^{2-/3-}$, the electrode reaction kinetics for $MV^{+2/+}$ are relatively insensitive to the physicochemical properties of both $sp^2$-bonded carbon and diamond electrodes (Granger, M. C., et al., *Anal. Chem.* 72, 3793 (2000); Wang, J., et al., *New Diamond Front. Carbon Technol.* 9, 317 (1999); and Qiu, F., et al., *Anal. Chem.* 72, 2362 (2000)). The kinetics are mainly influenced by the density of electronic states at the formal potential. In fact, good responsiveness was also observed for the $MV^{+1/0}$ redox couple at an even more negative potential of −950 mV. The cathodic peak at −1025 mV is associated with the reduction of $MV^{+\bullet}$ to $MV^{\circ}$. The peak shape is consistent with a diffusion-limited reaction. However, the corresponding oxidation peak at −1010 mV for the $MV^{\circ}$ to $MV^{+\bullet}$ transition does not have the shape expected for a diffusion-limited process but, rather, is sharp and narrow, consistent with an oxidative desorption event. $MV^{\circ}$ has limited solubility in aqueous media, and depending on the solution conditions, MV concentration and the electrode surface properties, $MV^{\circ}$ can adsorb and accumulate on the electrode surface (Engelman, E. E., et al., *Langmuir*, 8, 1637 (1992)). This is the case presently. The sharp oxidation peak results from the oxidative desorption of surface-confined $MV^{\circ}$.

The cyclic voltammetric i-E curves for 4-tert-butyl-catechol (t-BC) and $Fe^{3+/2+}$ have much larger $\Delta E_p$'s and more asymmetric peak shapes. $\Delta E_p$'s of 419 and 679 mV are observed for t-BC and $Fe^{3+/2+}$. The asymmetry for t-BC and $Fe^{3+/2+}$, respectively. The $i_p^{ox}/i_p^{red}$ ratios are 1.8 and 0.91 for t-BC and $Fe^{3+/2+}$. The asymmetry for t-BC is particularly evident—this is due to the transfer coefficient being <0.5. The larger peak separations, as compared to the other four redox analytes, are due to more sluggish electrode reaction kinetics (Granger, M. C., et al., *Anal. Chem.* 72, 3793 (2000); and Wang, J., et al., *New Diamond Front. Carbon Technol.* 9, 317 (1999)). The catechol redox reaction involves the transfer of both electrons and protons, and the electrode kinetics are highly sensitive to the surface microstructure, the presence of surface carbon-oxygen functionalities, and the surface cleanliness of $sp^2$-bonded carbon electrodes (Chen, P., et al., *Anal. Chem.* 68, 3958 (1996)). Surface adsorption appears to lower the reorganization energy for this analyte. In other words, adsorption increases the reaction kinetics (Hunt DuVall, S., et al., *Anal. Chem.* 71, 4594 (1999)). It is supposed that the slow kinetics for diamond result from a lack of adsorption on the $sp^3$-bonded, hydrogen-terminated surface. Recent results have demonstrated a clear correlation between the fraction of exposed $sp^2$-bonded carbon in microcrystalline and nanocrystalline diamond films and the surface coverage of adsorbed catechols. The greater the coverage is, the smaller $\Delta E_p$ is.

The electrode kinetics for $Fe^{3+/2+}$ are strongly influenced by the presence of surface carbon-oxygen functional groups, specifically carbonyl groups, which catalyze the reaction on $sp^2$-bonded electrodes (McDermott, C. A., et al., *J. Electrochem. Soc.* 140, 2593 (1993)). The hydrogen-terminated diamond surface is void of such functionalities, so this is the postulated reason for the sluggish kinetics. Increasing the surface oxygen content on diamond has been observed to slightly decrease the $\Delta E_p$ (Yagi, I., et al., *J. Electroanal. Chem.* 173, 473 (1999)).

FIG. 7 presents plots of $i_p^{ox}$ versus $v^{1/2}$ for the different redox analytes. It can be seen that the oxidation peak current for each redox system varies linearly with the scan rate$^{1/2}$ with a near-zero y-axis intercept, indicative of reactions limited by semi-infinite linear diffusion of reactants to the electrode surface. The quasi-reversible to reversible voltammetry for all the couples indicates that the boron-doped nanocrystalline diamond has a sufficient charge-carrier density over the wide potential range, a prerequisite for all redox reactions, to support a rapid electron transfer.

The electrical conductivity of previously reported nanocrystalline diamond thin-film electrodes, both as deposited and as deposited with incorporated nitrogen, largely results from the Π-bonding in the intercrystalline grain boundaries (Chen, Q., et al., *J. Electrochem. Soc.* 148, 44 (2001)). If this Π-bonding is removed, then the localized density of electronic states is reduced and the electrical conductivity decreases significantly. Hence, the electrochemical responsiveness of these films depends, to a great extent, on the chemical and electronic properties of the grain boundaries. The electrochemical responsiveness of the boron-doped nanocrystalline thin films should be much less influenced by the chemical and electronic properties of the grain boundaries. The diamond grains themselves should be highly conducting due to the carriers provided by the substitutionally inserted boron dopant atoms. To test this, an acid washing and hydrogen plasma treatment was applied, which is very effective at oxidatively removing $sp^2$-bonded carbon (Granger, M. C., et al., *Anal. Chem.* 72, 3793 (2000)). The first step involved immersing the films in warm aqua regia for 30 minutes. The films were then rinsed with ultrapure water. The second step involved exposing the samples to a warm solution of $H_2O_2$ (30%) for 30 min. This was followed by rinsing with ultrapure water and then drying. The films were then hydrogen-plasma-treated (microwave-assisted) for 30 min to remove the surface oxides formed during the acid washing and to terminate the surface with hydrogen (Granger, M. C., et al., *Anal. Chem.* 72, 3793 (2000); and Granger, M. C., et al., *J. Electrochem. Soc.* 146, 4551 (1999)). The hydrogen was introduced into the reactor at flow rate of 200 sccm. The plasma power, system pressure, and temperature were 1 kW, 35 Torr, and 800° C., respectively.

The electrochemical response of two nanocrystalline films was evaluated before and after the acid washing/hydrogen-plasma treatment. One was a nanocrystalline film deposited in the presence of the boron dopant source and the other was a nanocrystalline film deposited without any intentional boron dopant added. The response for the boron-doped nanocrystalline film was unaffected by the chemical/plasma treatment. A nearly reversible response was observed for $Fe(CN)_6^{3-/4-}$ with a $\Delta E_p$ of 78 mV before and 72 mV after treatment. A nearly reversible response was also observed for $Ru(NH_3)_6^{3+/2+}$, $IrCl_6^{3-/4-}$, and methyl viologen with $\Delta E_p$'s of 74, 71, and 59 mV, respectively, after treatment. The response of the nanocrystalline film, deposited without intentionally added boron, was altered by the treatment. The $\Delta E_p$ for $Ru(NH_3)_6^{3+/2+}$ increased to 165 mV after treatment. The $\Delta E_p$'s for $Fe(CN)_6^{3-/4-}$, $IrCl_6^{3-/4-}$ and $MV^{2+/+}$ all increased after treatment to 166, 83, and 99 mV, respectively. A decrease in the electrical conductivity, due to a decrease in the Π-bonded carbon in the grain boundaries, causes the increase in $\Delta E_p$. The $\Delta E_p$ increases for this particular nanocrystalline film were not as dramatic as we have seen in tests of other films. The reason is that this film, even though deposited with no intentionally added boron, was doped to some extent because it was prepared in a reactor that is regularly used for depositing boron-doped films. In fact, recent boron nuclear-reaction analysis measurements of an "undoped" film, deposited in the same reactor, revealed a doping level of ca. 50 ppm B/C. Previous tests have shown that the electrochemical response of an undoped nanocrystalline film can almost be completely inhibited after the same chemical/plasma treatment. Even though not as dramatic, the present results suggest that the electronic properties of the boron-doped films are dominated by the acceptor concentration in the diamond lattice rather than by the physicochemical properties of the grain boundaries.

Electroanalysis. Two analytical applications using these electrodes were investigated. First, these electrodes were observed to be useful for the quantitative electrooxidation of aliphatic polyamines (Koppang, M., et al., *Anal. Chem.* 71, 1188 (1999); and Witek, M. A., et al., *Anal. Chim. Acta*, 440, 119 (2001)). Second, they were used for the detection of trace metal ions. Heavy metal contamination in the environment is a growing concern. Anodic-stripping voltammetry is effective for the multicomponent analysis of metal-containing solutions due to the technique's high sensitivity and selectivity (Wang, J., *stripping Analysis: Principles, Instrumentation and Applications;* VCH Publishers: Weinheim, FRG, (1985)). Mercury and mercury-coated electrodes function well as the working electrode, but the metal is highly toxic and there is much interest in finding alternate, nontoxic electrode materials. Hydrogen-terminated diamond is one of these alternative electrodes that has very attractive features for this application: (Granger, M. C., et al., *Anal. Chim. Acta*, 397, 145 (1999)) (i) a large overpotential for hydrogen evolution, (ii) an overpotential for the reduction of oxygen, (iii) a stable surface chemistry and microstructure, (iv) a chemically inert surface that resists fouling, and (v) no metal-diamond chemical interactions.

Metal deposition on diamond is an immensely complicated process and is not fully understood. First, a particular metal under study must nucleate and grow on the surface. The sites at which this occurs, as well as the nucleation and growth mechanism for many metals, is unknown. Copper deposits equally well on both the facets and grain boundaries of highly boron-doped microcrystalline diamond. The metal deposits by an instantaneous nucleation and growth mechanism at low overpotentials and by progressive mechanism at high overpotentials. Silver deposits on microcrystalline diamond have also been studied (Vinokur, N., et al., *J. Electrochem. Soc.* 146, 125 (1999)). At low overpotentials, an instantaneous nucleation and growth mechanism is observed, whereas at high overpotentials, a progressive mechanism is operative. Zinc deposits on microcrystalline diamond by a progressive mechanism at both low and high overpotentials.

Second, when multiple metals are deposited simultaneously, as is the case in a real stripping voltammetric measurement, not only is their interaction with the diamond surface important but equally critical is their interaction with each other. There is a possibility of intermetallic compounds or alloys forming, both which will affect the oxidation or stripping potential for each. When these heterogeneous deposits form, the oxidation of a particular metal can occur from different sites on the diamond surface or from another metal surface. Oxidation from these multiple sites leads to peak broadening due to a spread in reaction kinetics. Ideally, for this application, highly dispersed metal deposits of low volume, without any intermetallic interactions, are desired. Even with these complexities, we suppose that diamond may be a useful electrode for the determination of trace metal ions via anodic-stripping voltammetry (Granger, M. C., et al., *Anal. Chim. Acta*, 397, 145 (1999); Manivannan, A., et al., *Electrochem. Solid State Lett.* 2, 454 (1999); and Prado, C., et al., *Electroanal.* 14, 262 (2002)).

A summary of the individual metal ion detection figures of merit for the determination of Ag(I), Cu(II), Pb(II), Cd(II), and Zn(II) by anodic-stripping voltammetry is given in Table 3. The preconcentration step involved the application of −1200 mV for 3 min (no stirring). The oxidation peaks occurred at ca. 400, 110, −450, −710, and −1010 mV versus Ag/AgCl for 100 μM solutions of Ag(I), Cu(II), Pb(II), Cd(II), and Zn(II) and shifted positive with increasing solution concentration (i.e., increasing surface coverage). The limit of quantitation for the individual metals is in the low ppb range. The limit of quantitation is highest for Zn, and this is due, at least to some extent, to the hydrogen-evolution reaction interfering with the coulometric efficiency of the metal deposition. Good response precision and stability (<4%) are seen for all five metals.

TABLE 3

Summary of the Aodic-Stripping Voltammetric Data for Individual Metal Ions at a Boron-doped Nanocrystalline Diamond Thin-Film Electrode

| parameter | linear dynamic range (ppb) $r^2 > 0.99$ | Limit of quantitation (ppb) (S/N > 3) | sensitivity (μC/ppb) | response precision (%) (n = 10) | response stability (%) (3-day test) |
|---|---|---|---|---|---|
| Ag (I) | 0.1–10000 | 0.11 | 0.111 | 0.92 | 3.87 |
| Cu (II) | 0.6–6400 | 0.64 | 0.045 | 1.88 | 4.87 |
| Pb (II) | 2–20000 | 2.07 | 0.050 | 0.50 | 1.67 |
| Cd (II) | 1.1–11000 | 1.12 | 0.099 | 1.30 | 3.37 |
| Zn (II) | 6.5–6500 | 6.54 | 0.035 | 3.39 | 3.83 |

In another series of more "real world" experiments, solutions containing mixtures of Cd(II), Pb(II), and Ag(I) were analyzed using the same experimental conditions. FIG. 8 shows anodic-stripping voltammograms for metal ion concentrations ranging from 0.01 to 10 μM. The deposition was performed at −1000 mV for 3 min (no stirring). The peaks were identified based on the stripping peak potentials for the individual metals. It can be seen that the oxidation peak potentials shift positive and increase in width with increasing solution concentration (i.e., increasing surface coverage). Also, the Pb (II) stripping peak splits into two fractions. The more negative component is apparent at higher solution concentrations, although the ratio of the two remain constant with increasing coverage. One possible explanation for this split is metal stripping from two different sites on the electrode. For example, the Pb may be oxidizing from a homogeneous deposit on the diamond surface and heterogeneous sites where multiple metals have co-deposited. Another possibility is the formation of an intermetallic compound. In a series of separate experiments, it was observed that standard additions of either Cu(II) or Ag(I) to a test solution of Pb(II) resulted in the formation of two Pb(II) stripping peaks. Therefore, it is supposed that the dual Pb(II)-stripping peaks, observed presently, are caused by the formation of a Ag—Pb intermetallic compound.

It is also observed that the Cd(II)-stripping peak charge is suppressed when co-deposited with Ag(I). Even though equimolar amounts of Pb(II) and Cd(II) are present in solution, the stripping charge for Cd(II) is significantly less than that for Pb(II). It was observed, in a series of additional experiments, that the addition of Ag(I), Pb(II), or Cu(II) to a solution containing Cd(II) caused some suppression of the Cd(II)-stripping peak, with the greatest suppression seen after the addition of Ag(I). In fact, in the presence of Cd(II), the stripping charge for Ag(I) is enhanced, suggesting that some of the deposited Cd is stripping at the Ag oxidation potential. Therefore, the suppression of the Cd(II) peak is attributed to the formation of an Ag—Cd intermetallic compound.

Even with the complications associated with the suspected intermetallic compound formation, the linear dynamic range extended from 0.01 to 100 μM for Cd(II) and Pb(II) with linear regression correlation coefficients of 0.992 each, and from 0.001 to 50 μM for Ag(I) with a linear regression correlation coefficient of 0.994. The limit of quantitation for Ag(I), Pb(II), and Cd(II) in the mixture was 0.01 μM or 1,2, and 1 ppb respectively, at which the S/N ratio of the Cd(II) peak was just over 3:1. Ag(I) and Pb(II) still showed a good S/N (~30:1) at this concentration.

CONCLUSIONS

Boron-doped nanocrystalline diamond thin films were deposited by CVD from an $CH_4/H_2/Ar$ source gas mixture. Born doping was accomplished either using a solid-state diffusion source or $B_2H_6$ added to the source gas mixture. XRD revealed that the bulk crystal structure of the deposited film is cubic diamond. TEM indicated the film consists of 10~15 nm randomly oriented but atomically ordered diamond grains. SEM showed these grains form aggregates ~50–100 nm in size. Large water contact angles indicated the surface is hydrophobic, consistent with a hydrogen surface termination.

The films exhibited a wide working potential window, a low voltammetric background current, and good responsiveness for $Fe(CN)_6^{3-/4-}$, $Ru(NH_3)_6^{2+/3+}$, $IrCl_6^{2-/3-}$, and methyl viologen without any pretreatment. The quasi-reversible voltammetry for all the couples indicates that the boron-doped nanocrystalline diamond has a sufficient density of electronic states over the wide potential range to support rapid electron transfer. More sluggish electrode kinetics were found for 4-tert-butyl-catechol and $Fe^{3+/2+}$. The sluggish kinetics for the former are attributed to weak surface adsorption, and the latter, at least partially, to the absence of catalyzing surface carbonyl functional groups. Boron-doped nanocrystalline films were found to be useful for the detection of trace metal ions, such as Ag(I), Cu(II), Cd(II), Pb(II), and Zn(II). The detection of the metal ions in solution mixtures is, however, complicated by intermetallic compound formation.

Most importantly, the electrical conductivity of the films is not affected by changes in the physicochemical properties of the grain boundaries, but rather is dominated by the charge carried within the diamond due to the substitutionally inserted boron dopant atoms.

The hydrogen termination occurs after application of our growth conditions ($H_2$ present in the source gas, which is a hydrogen poor environment). In general, it was found that the best and most reproducible electrochemical response was observed for the hydrogen terminated surface. Another surface termination can be used. For example, it is common in electrochemical environments to have an electrode surface terminated with oxygen functional groups.

In general, boron atoms in the gas phase are incorporated in the diamond film in two places—aggregated in grain boundaries and defects and substitutionally inserted into the growth diamond lattice. The substitutional boron is the type that is important electronically. Boron is a little smaller (atomic radius) than carbon so it can substitute at high levels without causing any distortion of the diamond lattice. It is this type of boron that influences the electronic properties by giving rise to an electron acceptor band very near the filled valence band of the diamond. Thermal energy promotes an electron from the filled valence band (highest occupied molecular orbital) to the unoccupied acceptor band. The empty electron "spot" in the valence band (a hole) as well as the free electron in the dopant band can move in an electric field and the material becomes conducting. The conductivity in these boron-doped nanocrystalline diamond films results in largest part from the hole concentration, and to a much lesser extent, from the pi-bonded grain boundaries. The major benefit of these materials, as compared to the nitrogen-doped ultrananocrystalline diamond is the fact that the electrical conducting is dominated by the substitutional boron and not the properties of the grain boundaries.

The following cyclic voltammetric i-E curves give some evidence for the through-grain electrical conduction in the boron-doped nanocrystalline diamond films. In Figure _A cyclic voltammetric i-E curves for a nitrogen-containing ultrananocrystalline diamond (UNCD) thin film in the presence of 0.3 mM $Ru(NH_3)_6^{+3/+2}$ in 1 M KCl. The potential sweep rate was 0.1 V/s. Two curves are presented. The curve with the largest peak currents and the smallest peak potential separation is for the UNCD film as deposited. The electrical conduction in this film (no boron doping) results exclusively from the Π-states in the bandgap caused by the $sp^2$ bonded carbon in the grain boundaries. The electrical conductivity of these films is sensitive to the physicochemical changes in the grain boundary carbon. The second curve is for the same film after exposing the film to a two-step chemical oxidation in warm HF (30 min) and warm 30% $H_2O_2$ (30 min). This chemical treatment introduced surface carbon-oxygen functionalities but also is effective at removing $sp^2$ bonded carbon from the grain boundaries. The film was also exposed to a hydrogen plasma treatment for ca. 15 min. This treatment replaces the surface oxygen with hydrogen and it converts $sp^2$ bonded carbon in the grain boundaries to $sp^3$ bonded carbon. Both of these treatments alter the properties of the grain boundary carbon and reduce the density of electronic states, i.e., reduces the electrical conductivity of the film. The voltammetric i-E curve for $Ru(NH_3)_6^{+3/+2}$ is expected to have reduced peak currents and an increased peak potential separation. This in fact what is observed as in FIG. 10A. FIG. 10B, on the other hand, shows cyclic voltammetric i-E curves for a boron-doped nanocrystalline diamond thin film, exposed to 1 mM $Ru(NH_3)_6^{+3/+2}$ in 1 M KCl, before and after the same treatment. If the electrical conduction is primarily through the grains rather than the grain boundaries, any alteration in the physicochemical properties of the grain boundaries should not significantly affect the electrical conductivity of the film, i.e., unchanging electrochemical response. This is in fact observed. There is no change in the peak potential separation or the peak currents. This simple experiment gives credence to the theory that the electrical conduction in the boron-doped materials is primarily through the grains.

It is intended that the foregoing description be only illustrative of the present invention and that the present invention be limited only by the hereinafter appended claims.

We claim:

1. A process for forming a nanocrystalline diamond electrode containing elemental boron in the crystals as a dopant in a concentration of at least about $10^{19}$ atoms/cm$^3$, an electrical conductivity of at least about $1(\Omega\ cm)^{-1}$ and wherein the conductivity is brought about by charge carriers introduced by boron, as opposed to boundaries between the crystals which comprises:

(a) chemically vapor depositing the diamond as a coating on the substrate, from a gaseous mixture of a boron compound, methane and argon, or methane, hydrogen and argon, onto a substrate which enables the formation of the nanocrystalline diamond; and (b) forming an electrode from the diamond coated substrate.

2. The process of claim 1 wherein the flow rates of $CH_3$, $H_2$ and Ar are about 1, 5 and 94 sccm, at a pressure of 140 Torr and at a temperature of about 800° C.

3. The process of claim 1 wherein after the depositing the diamond is exposed to hydrogen during cooling.

4. The process of claim 1 wherein in addition the diamond is exposed to oxygen during cooling.

5. The method of claim 1 wherein the diamond which is formed is heated in the presence of a hydrogen plasma after step (a).

* * * * *

UNITED STATES PATENT AND TRADEMARK OFFICE
CERTIFICATE OF CORRECTION

PATENT NO.         : 7,144,753 B2
APPLICATION NO. : 10/991272
DATED              : December 5, 2006
INVENTOR(S)        : Greg M. Swain et al.

It is certified that error appears in the above-identified patent and that said Letters Patent is hereby corrected as shown below:

Column 3, line 2, "$CH_3$." should be --$CH_3\bullet$--.

Column 7, line 24, "methyl viblogen" should be --methyl viologen--.

Column 11, line 65, "$i^{pox}/i_p^{red}$" should be --$i_p^{ox}/i_p^{red}$--.

Column 13, line 1, "$Fe^{3+2+}$" should be --$Fe^{3+/2+}$--.

Signed and Sealed this

Twenty-first Day of August, 2007

JON W. DUDAS
*Director of the United States Patent and Trademark Office*